US006585206B2

United States Patent
Metz et al.

(10) Patent No.: US 6,585,206 B2
(45) Date of Patent: Jul. 1, 2003

(54) MEDICAL ACCESSORY SUPPORT

(75) Inventors: Darrell L. Metz, Batesville, IN (US); John P. Biondo, Aurora, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 09/874,486

(22) Filed: Jun. 5, 2001

(65) Prior Publication Data

US 2002/0047075 A1 Apr. 25, 2002

Related U.S. Application Data

(60) Provisional application No. 60/209,379, filed on Jun. 5, 2000.

(51) Int. Cl.[7] ............................................. A47C 19/22
(52) U.S. Cl. ................. 248/229.1; 248/121; 248/125.7; 248/222.11; 248/289.11
(58) Field of Search ............................. 248/121, 122.1, 248/125.7, 222.13, 221.11, 289.11, 229.1; 5/503.1; 464/45, 46; 74/813 L, 813 R

(56) References Cited

U.S. PATENT DOCUMENTS

| | | | |
|---|---|---|---|
| 3,709,372 A | * | 1/1973 | Alexander .................. 211/74 |
| 3,709,556 A | | 1/1973 | Allard et al. |
| 4,190,224 A | * | 2/1980 | LeBlanc et al. ......... 248/227.3 |
| 4,225,104 A | | 9/1980 | Larson |
| 4,332,378 A | * | 6/1982 | Pryor ......................... 135/67 |
| 4,489,454 A | * | 12/1984 | Thompson ............. 248/289.11 |
| 4,807,837 A | * | 2/1989 | Gawlik et al. .............. 211/196 |
| 4,811,435 A | | 3/1989 | Foster et al. |
| 4,886,237 A | * | 12/1989 | Dennis .................. 248/289.11 |
| 4,905,944 A | * | 3/1990 | Jost et al. ................ 248/125.8 |
| 5,060,327 A | | 10/1991 | Celestina et al. |
| 5,072,906 A | | 12/1991 | Foster |
| 5,078,348 A | * | 1/1992 | Babitchenko ............... 211/196 |
| 5,117,521 A | | 6/1992 | Foster et al. |
| 5,135,191 A | * | 8/1992 | Schmuhl .................. 248/125.1 |
| 5,319,816 A | | 6/1994 | Ruehl |
| 5,335,384 A | | 8/1994 | Foster et al. |
| 5,335,651 A | | 8/1994 | Foster et al. |
| 5,337,845 A | | 8/1994 | Foster et al. |
| 5,337,992 A | * | 8/1994 | Pryor et al. .............. 248/125.1 |
| 5,366,191 A | | 11/1994 | Bekanich |
| 5,388,294 A | | 2/1995 | Reeder |
| 5,407,163 A | | 4/1995 | Kramer et al. |
| 5,421,548 A | * | 6/1995 | Bennett et al. ............. 248/129 |
| 5,457,831 A | | 10/1995 | Foster et al. |
| 5,497,766 A | | 3/1996 | Foster et al. |
| 5,499,721 A | * | 3/1996 | Hansen et al. .............. 211/113 |
| 5,527,289 A | | 6/1996 | Foster et al. |
| 5,561,878 A | | 10/1996 | Ruehl |
| 5,562,091 A | | 10/1996 | Foster et al. |
| 5,636,823 A | | 6/1997 | Boyd |
| 5,647,491 A | | 7/1997 | Foster et al. |
| 5,802,636 A | | 9/1998 | Corbin et al. |
| 5,806,111 A | | 9/1998 | Heimbrock et al. |
| 5,898,961 A | | 5/1999 | Ambach et al. |
| 5,966,760 A | | 10/1999 | Gallant et al. |
| 6,179,260 B1 | * | 1/2001 | Ohanian .................. 248/219.4 |

FOREIGN PATENT DOCUMENTS

WO     WO 97/49442     12/1997

* cited by examiner

*Primary Examiner*—Leslie A. Braun
*Assistant Examiner*—Ingrid Weinhold
(74) *Attorney, Agent, or Firm*—Bose McKinney & Evans LLP

(57) ABSTRACT

An accessory support apparatus for use with a patient support includes a body including a plurality of accessory couplers. A coupler is configured to couple the body to the patient support for pivotable movement about an axis of rotation. A latch is configured to lock the body selectively in one of a plurality of different positions relative to the patient support.

40 Claims, 5 Drawing Sheets

MEDICAL ACCESSORY SUPPORT

This application claims the benefit of U.S. Provisional Application No. 60/209,379, filed on Jun. 5, 2000, which is expressly incorporated herein by reference.

BACKGROUND AND SUMMARY OF THE INVENTION

The present invention relates to patient support and transport devices such as hospital beds, carts, chairs, and stretchers. More particularly, the present invention relates to supports that couple medical accessories to patient supports.

The treatment of patients, whom are restricted to hospital beds, carts, stretchers and other patient support and transport devices, may require the administration of medications intravenously using IV bags supported by IV poles with or without infusion pumps and, in some cases, the administration of supplemental oxygen. It is known to provide patient supports having IV pole supports. See, for example, U.S. Pat. Nos. 5,319,816 and 5,407,163.

In an illustrated embodiment of the present invention, an accessory support apparatus for use with a patient support comprises a body including a plurality of accessory couplers, a coupler configured to couple the body to the patient support for pivotable movement about an axis of rotation, and a latch configured to lock the body selectively in one of a plurality of different positions relative to the patient support.

In one embodiment, the apparatus includes a push handle coupled to one of the accessory couplers. The push handle includes a grip portion to permit a caregiver to move the patient support. In another illustrated embodiment, an IV pole is coupled to the push handle.

In another illustrated embodiment of the present invention, an apparatus for use with a patient support comprises a first member coupled to the patient support, a second member movably coupled to the first member, and a handle coupled to the first member. The second member includes an item holder.

In an illustrated embodiment, the first member is an outer telescoping member and the second member is an inner telescoping member which is movable relative to the outer telescoping member to adjust a position of the inner telescoping member. The apparatus also includes a coupler configured to lock a position of the inner telescoping member relative to the outer telescoping member.

In another illustrated embodiment, the handle is movable relative to the first member. A stop is illustratively coupled to the first member, and the handle is movable between the stop and the patient support. In one embodiment, the handle is configured to surround the first member. Therefore, the handle is slidable over the first member to permit the caregiver to adjust a position of the handle to a desired position on the first member.

In yet another illustrated embodiment, an apparatus for use with a patient support comprises a push handle including a grip portion to permit a caregiver to move the patient support, a coupler configured to couple the push handle to the patient support, and an IV pole coupled to the push handle.

In an illustrated embodiment, the push handle includes an outer telescoping member and the IV pole is an inner telescoping member which is movable relative to the outer telescoping member to adjust a position of the inner telescoping member relative to the push handle. In one embodiment, the push handle includes a grip portion which is movable relative to the outer telescoping member.

In another illustrated embodiment, a body is coupled to the push handle. The coupler is configured to couple the body to the patient support for pivotable movement about an axis of rotation. A latch is configured to lock the body selectively in one of a plurality of different positions relative to the patient support.

Additional features of the disclosure will become apparent to those skilled in the art upon consideration of the following detailed description when taken in conjunction with the accompanying drawings.

BRIEF DESCRIPTION OF THE DRAWINGS

The detailed description particularly refers to the accompanying figures in which.

DETAILED DESCRIPTION OF THE DRAWINGS

Figure 1:
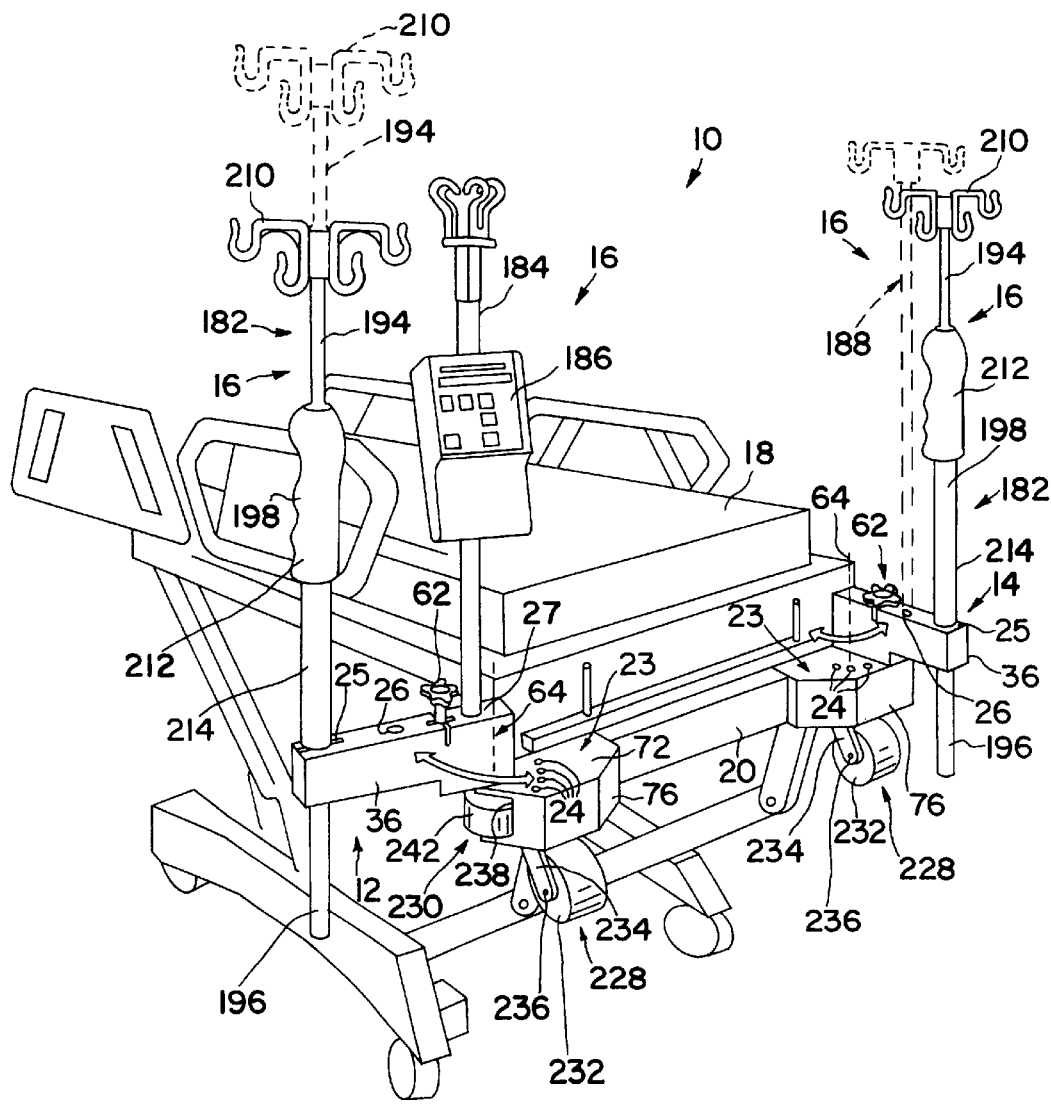
FIG. 1 is a perspective view showing a hospital bed, a pair of accessory supports coupled to a frame of the hospital bed, and several IV poles coupled to the accessory supports.
Figure 2:
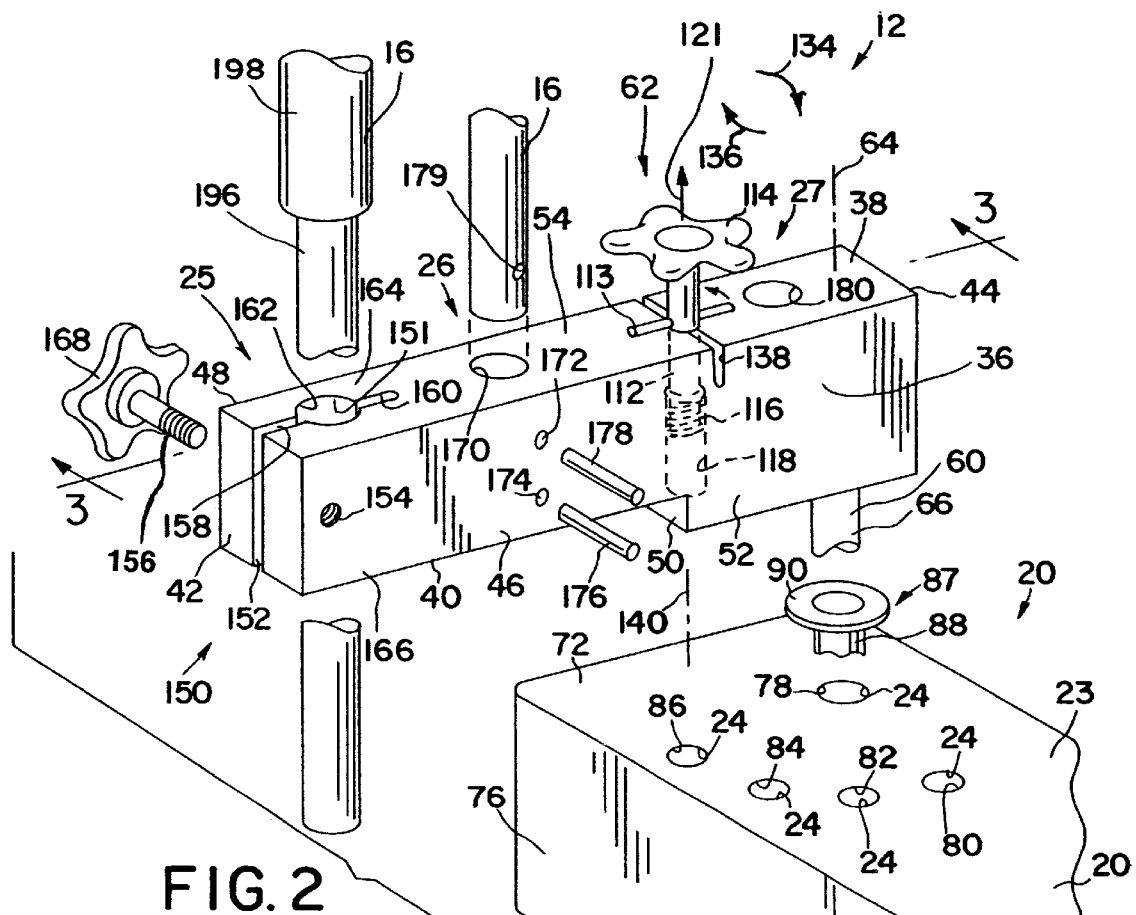
FIG. 2 is an exploded perspective view of one of the accessory supports of FIG. 1 and a portion of the frame of the hospital bed showing the accessory support including a body positioned above the portion of the frame and a clutch positioned beneath the portion of the frame.

As shown in FIG. 1, a hospital bed or patient support 10 is provided along with accessory supports 12, 14 coupled to hospital bed 10 and a plurality of accessories 16 coupled to supports 12, 14. The hospital bed 10 includes a patient support surface 18 and a frame 20. The frame 20 includes a plurality of apertures 24 formed in its upper surface 22 as shown in FIG. 2. The apertures 24 in frame 20 act as couplers which assist in coupling accessory supports 12, 14 to hospital bed 10. In the illustrated embodiment, the apertures 24 are formed in two corners of frame 20 at bracket coupling locations 23 as shown in FIG. 1. Multiple apertures 24 are formed in each of these bracket coupling locations 23 so that accessory supports 12, 14 may be coupled to frame 20 in a plurality of positions as shown, for example, in FIG. 5.

Figure 6:
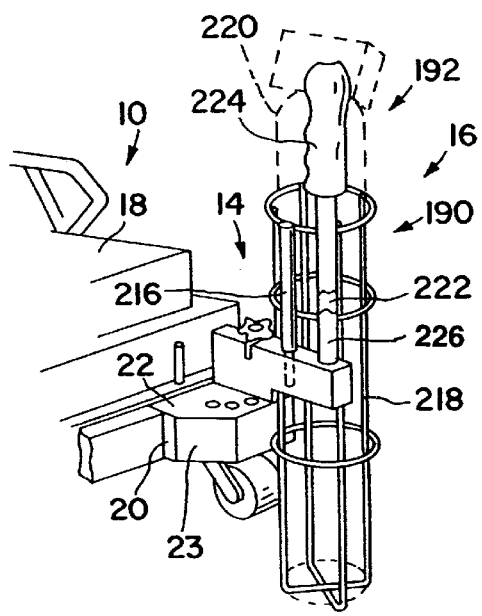
FIG. 6 is a perspective view showing an oxygen tank holder and a push handle coupled to an accessory support.

The accessory supports 12, 14 include a plurality of couplers 25, 26, 27 which assist in coupling the accessories 16 to hospital bed 10. These couplers 25, 26, 27 interact with accessories 16 so that accessory supports 12, 14 support accessories 16 as shown in FIG. 1. Typical accessories 16 may include IV pole/handle devices, IV poles, handles, infusion pumps, and oxygen tank holders as shown in FIGS. 1 and 6. In addition, other accessories (not shown) such as voice actuated patient control units, computer equipment, monitor screens, traction equipment, and patient assist bars may be coupled to supports 12, 14.

Figure 3:
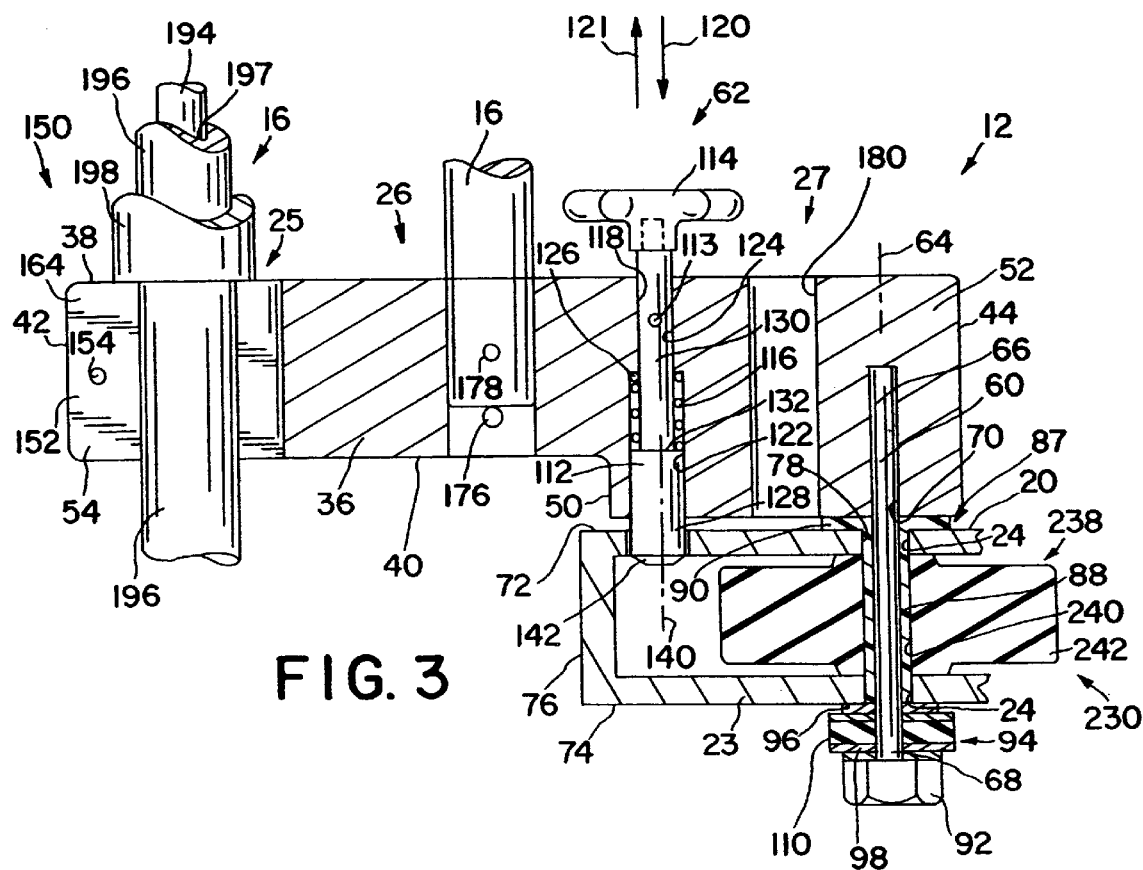
FIG. 3 is a sectional view of the frame and accessory support taken along line 3—3 of FIG. 2.

Each of the accessory supports 12, 14 includes a body 36 having spaced-apart upper and lower surfaces 38, 40, spaced-apart end surfaces 42, 44 extending between upper and lower surfaces 38, 40, and spaced-apart side surfaces 46, 48 extending between upper and lower surfaces 38, 40 and end surfaces 42, 44 as shown, for example, in FIGS. 2 and 3. In the illustrated embodiment, all of these surfaces are flat planar surfaces except for the lower surface 40. The lower surface 40 includes a step 50 which defines first and second portions 52, 54 of body 36, having height dimensions 56, 58, respectively. In alternative embodiments, the lower surface of the body is a substantially flat planar surface.

Each of the accessory supports 12, 14 also includes a coupler or pivot post 60 and a retainer or latch 62 configured to couple body 36 of accessory supports 12, 14 to frame 20. The pivot post 60 defines an axis 64 about which accessory support 12, 14 rotates relative to frame 20 as shown, for example, in FIG. 5. The pivot post 60 permits the accessory support 12, 14 to rotate about axis 64 to a desired position and latch 62 locks the accessory support 12, 14 in the desired position as shown in FIG. 3.

As shown in FIG. 2, the pivot post 60 includes an upper portion 66 coupled to the body 36 of accessory support 12, 14 and a threaded lower portion 68 spaced apart from body 36. In the illustrated embodiment, the upper portion 66 of the pivot post 60 is press fit into a bore 70 formed in the body 36 and the lower portion 68 extends through bracket coupling location 23.

The frame 20 at each bracket coupling location 23 includes spaced-apart upper and lower walls 72, 74 and a side wall 76 extending between the upper and lower walls 72, 74 as shown in FIG. 2. The plurality of apertures 24 formed in the frame 20 at each bracket coupling location 23 include a pivot post aperture 78 extending between upper and lower walls 72, 74 and first, second, third, and fourth latch position apertures 80, 82, 84, 86 formed in the upper wall 72 as shown in FIGS. 2 and 3.

Each pivot post 60 of accessory supports 12, 14 is positioned in a respective pivot post aperture 78. A bushing 87 is also positioned in each pivot post aperture 78 between pivot post 60 and frame 20. Each bushing 87 includes a cylindrical sleeve 88 positioned in pivot post aperture 78 and an annular disk 90 positioned between upper wall 72 of frame 20 and lower surface 40 of body 36 of accessory support 12, 14 as shown in FIGS. 2 and 3. The bushings 87 minimize the contact between frame 20 and accessory supports 12, 14 to minimize wear of frame 20 and accessory supports 12, 14. In the illustrated embodiment, the pivot post 60 includes a uniform diameter along its length. In alternative embodiments, the pivot post includes a diameter that varies along its length. For example, in alternative embodiments, the portion of pivot post positioned in the body of the accessory support may be smaller in diameter than the portions of the pivot post that are positioned outside of the accessory support. In such an alternative embodiment, it will be appreciated that the larger diameter portion of the pivot post defines a shoulder which abuts the lower surface of the body of the accessory support.

Threaded lower portion 68 of pivot post 60 is coupled to frame 20 by a nut 92, clutch 94, and washer 96, as shown in FIGS. 2 and 3. The nut 92, as shown in FIG. 3, is screwed onto lower portion 68 of pivot post 60 to secure washer 96 and clutch 94 between nut 92 and the lower wall 74 of frame 20. Clutch 94 includes washers 98 and a resilient pad 110 that is positioned between the washers 98. In preferred embodiments, resilient pad 110 is made from a fiber, plastic, or resinous material. In alternative embodiments, the clutch is replaced by a bushing or bearing.

A caregiver may increase or decrease the resistance to relative pivoting movement of supports 12, 14 and frame 20 by tightening or loosening nut 92. When supports 12, 14 are not locked by latch 62 relative to frame 20, clutch 94 holds supports 12, 14 in a desired position with respect to bed 10, but still allows supports 12, 14 to pivot about axis 64 in response to a sufficient amount of force applied to supports 12, 14 or to any of the equipment or accessories 16 coupled to supports 12, 14. Accordingly, if supports 12, 14 are not secured by latch 62 and are subjected to incidental contact, such as being struck by or striking an object, supports 12, 14 will yield by pivoting about axis 64 to prevent or minimize damage to supports 12, 14 and to any accessories 16 or equipment carried by supports 12, 14.

Figure 4:
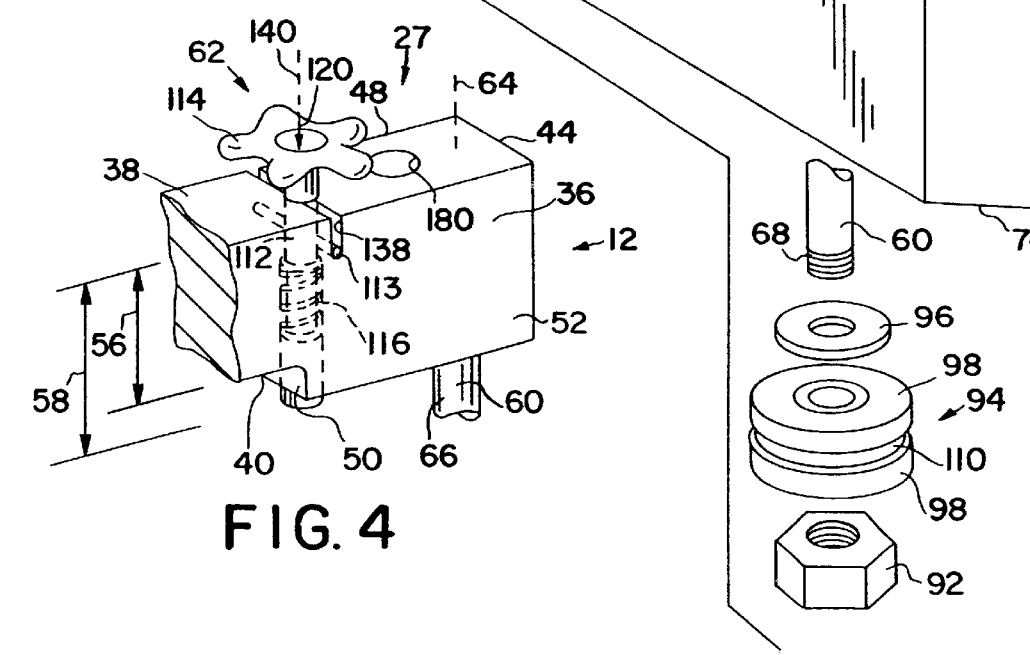
FIG. 4 is a perspective view of a portion of the accessory support showing the accessory support including a latch in a "locked" position.

As previously mentioned, the latches 62 of supports 12, 14 assist in fixing the position of supports 12, 14 relative to frame 20. Each spring-biased latch 62 includes a locking pin 112, a handle 114 coupled to locking pin 112, a position pin 113 coupled to locking pin 112, and a spring 116 as shown in FIGS. 2–4. The locking pins 112 are received in latch position apertures 80, 82, 84, 86 of frame 20 to lock the position of supports 12, 14 in a selected location relative to bed 10.

Each support 12, 14 includes a latch aperture 118 extending between upper and lower surfaces 38, 40 of body 36 of support arm 12, 14 for receiving locking pin 112 and spring 116 as shown in FIGS. 2–4. The spring 116 biases the locking pin 112 downwardly in direction 120 so that locking pin 112 is biased downwardly in direction 120 into a latch position aperture 80, 82, 84, 86 of frame 20 when the locking pin 112 is lined up with a latch position aperture 80, 82, 84, 86.

The latch aperture 118 of frame 20 and locking pin 112 are shaped to aid spring 116 in biasing locking pin 112 downwardly in direction 120. Each latch aperture 118 includes a larger diameter, lower portion 122 and a smaller diameter, upper portion 124 separated from the larger diameter portion 122 by a stepped surface 126. Each locking pin 112 includes a larger diameter, lower portion 128 and a smaller diameter, upper portion 130 separated from the larger diameter portion 128 by a stepped surface 132. The locking pin 112 is inserted into the lower opening of aperture 118 so that the stepped surfaces 126, 132 of the aperture 118 and locking pin 112, respectively, oppose or face each other and entrap spring 116.

The handle 114 assists a user in moving the locking pin 112 between a locked position, as shown in FIG. 4, wherein the locking pin 112 extends into a latch position aperture 80, 82, 84, 86 of frame 20 to lock the position of the support 12, 14 relative to the bed 10 and an unlocked position wherein the locking pin 112 does not extend into a latch position aperture 80, 82, 84, 86 of frame 20 to permit support 12, 14 to be pivoted about axis 64 relative to the bed 10. As shown in FIG. 3, handle 114 is coupled to an upper end of locking pin 112 to assist a user in moving locking pin 112 vertically in directions 120, 121 and about axis 64 in directions 134, 136.

The position pin 113 maintains the locking pin 112 in the unlocked position. As best shown in FIG. 2, the position pin 113 is coupled to the small diameter portion 130 of locking pin 112. First portion 52 of support 12, 14 is formed to include a slot 138 that intersects latch aperture 118 and is sized to receive position pin 113. Slot 138 is open at upper surface 38 of body 36 of support 12, 14 and extends into body 36. In the illustrated embodiment, slot 138 extends between and is open at side surfaces 46, 48 of body 36.

In the locked position, shown in FIG. 3, the locking pin 112 is positioned in a latch position aperture 80, 82, 84, 86 and the position pin 113 is positioned in slot 138. The spring 116 urges locking pin 112 downwardly in direction 120 to assist in maintaining locking pin 112 in the locked position. To move the locking pin 112 from the locked position to the unlocked position, a user grabs handle 114 and moves the locking pin 112 and position pin 113 upwardly in direction 121 until locking pin 112 is not positioned in a latch position aperture 80, 82, 84, 86 and the position pin 113 is not positioned in slot 138.

The user then rotates the handle 114 so that the locking pin 112 stays in the unlocked position as shown in FIG. 2. Once locking pin 112 and position pin 113 are removed from aperture 80, 82, 84, 86 and slot 138, respectively, the user may rotate the handle 114 in either direction 134, 136 so that position pin 113 is not aligned with slot 138. When the position pin 113 is rotated in this manner, the user may release handle 114 and the spring 116 will urge position pin 113 downwardly in direction 120 so that position pin 113 abuts the upper surface 38 of body 36 of support 12, 14 as shown in FIG. 2. When the position pin 113 abuts the upper surface 38 of body 36, the locking pin 112 is held in its unlocked position above the lower surface 40 of body 36 of support 12, 14. It will be appreciated that, when locking pins 112 are in their unlocked positions, the locking pins 112 may protrude slightly beneath the lower surface 40 of support 12, 14 without locking the position of supports 12, 14 relative to frame 20 due to the thickness of annular disk 90 of bushings 87.

Figure 5:
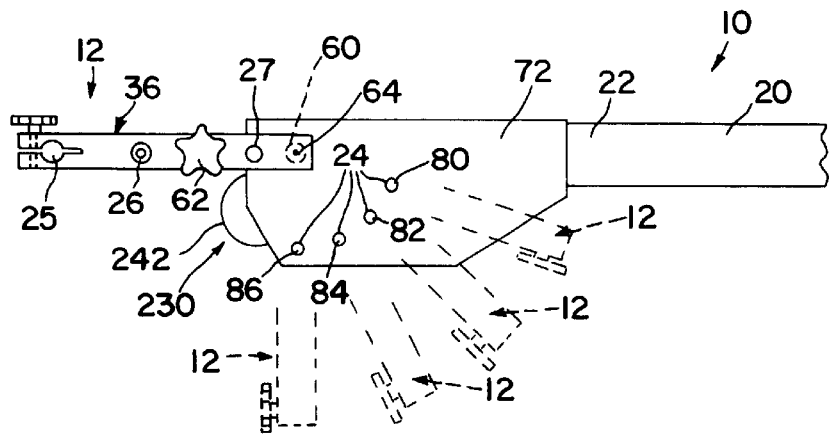
FIG. 5 is a top plan view of the accessory support and a portion of the frame of the hospital bed showing, in phantom, a plurality of positions in which the accessory support is lockable relative to the hospital bed.

After locking pin 112 is placed in the unlocked position, the support 12, 14 may be pivoted about axis 64 to a desired position relative to frame 20. Supports 12, 14 are individually positioned about their respective pivot axes 64 in one of a plurality of positions as shown in FIGS. 1 and 5. FIG. 1 shows one support 12 extending substantially transversely out to the side of bed 10 and the other support 14 extending longitudinally away from the end of bed 10. A caregiver moves supports 12, 14 to the side of bed 10 when increased access to a patient's head located at the head end of bed 10 is desired and when increased access to the equipment 16 supported by supports 12, 14 is desired by the caregiver standing alongside bed 10. Four latch position apertures 80, 82, 84, 86 are provided in the illustrated embodiment. However, in alternative embodiments, any number of latch position apertures can be used as desired to provide for any number of positions wherein the position of the accessory support is fixed relative to the frame.

Once the caregiver sets the desired position of the support 12, 14 relative to frame 20, the locking pin 112 is moved from the unlocked position to the locked position. To move the locking pin 112 from the unlocked position to the locked position, the user raises the handle 114 in direction 121, rotates the handle 114 in either direction 134, 136 until the position pin 113 is aligned with slot 138, and then releases the handle 114 or permits the spring 116 to bias the handle 114 downwardly in direction 120 so that the position pin 113 is positioned in slot 138 and locking pin 112 is positioned in a latch position aperture 80, 82, 84, 86 or is abutting upper wall 72 of frame 20. If the locking pin 112 is abutting upper wall 72 of frame 20, the support 12, 14 may be moved about axis 64 until the locking pin 112 lines up with a latch position aperture 80, 82, 84, 86 and spring 116 biases locking pin 112 into aperture 80, 82, 84, 86. The latch position apertures 80, 82, 84, 86 are arranged along a circular arc having a center that is coincident with the pivot axis 64. Thus, rotating the support 12, 14 will result in the locking pin 112 lining up and extending into one of the apertures 80, 82, 84, 86. The lower end of locking pin 112 includes a chamfer 142 that assists locking pin 112 in "finding" and extending into a latch position aperture 80, 82, 84, 86. Position pin 113 is merely one example of a key structure that may be used to hold locking pin 112 in its locked and unlocked positions. In alternative embodiments, the position pin may be another type of structure such as a lug formed separately from or integrally with the locking pin.

The shape of the frame 20 and the adjacent structure of bed 10 are factors in determining the range through which supports 12, 14 may pivot. In addition, the size and shape of the accessories 16 and other equipment coupled to supports 12, 14 may affect the range of motion through which supports 12, 14 may pivot. That is, the range that each support 12, 14 may pivot about axis 64 relative to bed 10 could be limited by contact of the support 12, 14 or the accessories/equipment 16 coupled to support 12, 14 with the frame 20 of bed 10 or against the adjacent bed structure. In alternative embodiments, the shape of the frame is varied to increase or decrease the pivotal range of the accessory supports.

As previously mentioned, couplers 25, 26, 27 are provided to assist in coupling accessories 16 to bed 10. The coupler 25 of accessory supports 12, 14 is a clamp 150. The clamp 150 is defined by first and second jaws 164, 166 having an inner clamp surface 151 defining a slot 152. The clamp 150 further includes a threaded aperture 154 extending between side surfaces 46, 48 of body 36 and a threaded stud 156. The slot 152 opens into upper and lower surfaces 38, 40 and end surface 42 of body 36 and includes first and second narrow sections 158, 160 and a circular section 162 positioned between the narrow sections 158, 160. The first narrow section 158 opens into end surface 42 of body 36 and the circular section 162 and second narrow section 160 are positioned between the end surfaces 42, 44 and side surfaces 46, 48 of body 36. The threaded aperture 154 extends through the first narrow section 158 of slot 152.

To use coupler 25, an accessory 16 is positioned in circular section 162 of slot 152 and the stud 156 is threaded into threaded aperture 154 to cause the inner clamp surface 151 of jaws 164, 166 to abut and hold accessory 16. The position of the accessory 16 relative to the accessory support 12, 14 is established by holding the accessory 16 in the desired position and then threading the stud 156 into the aperture 154 to clamp accessory 16 in the desired position. To remove the accessory 16 from coupler 25 or merely change the position of the accessory 16 relative to the accessory support 12, 14, the stud 156 is unthreaded until the accessory 16 can be moved. A handle 168 is coupled to stud 156 to assist a user in gripping and rotating the stud 156.

The coupler 26 of accessory supports 12, 14 includes a first aperture 170 opening into upper surface 38 of body 36, second and third apertures 172, 174 opening into side surface 46 of body 36, and first and second pins 176, 178 as shown in FIG. 2. The first pin 176 is positioned in third aperture 174 as shown in FIG. 3, to establish the relative vertical position of an accessory 16 and accessory support 12, 14.

To use coupler 26, an accessory 16 that includes an aperture 179 is positioned in first aperture 170 such that the accessory 16 abuts and rests on the first pin 176. The second pin 178 is then inserted into second aperture 172 and aperture 179 to fix the rotational position of accessory 16 and accessory support 12, 14. In alternative embodiments, neither the first nor second pins is used and the accessory is held in the accessory support by its weight. In additional alternative embodiments, only one of the first and second pins is used.

The coupler 27 includes an aperture 180 opening into upper surface 38 of body 36 of accessory support 12, 14. To use coupler 27, an accessory 16 is simply positioned in aperture 180. Once the accessory 16 is positioned in aperture 180, the accessory is free to rotate relative to accessory support 12, 14 about its longitudinal axis.

Although circular shaped section 162 and apertures 170, 172, 174, 180 are illustrated for couplers 25, 26, 27, in alternative embodiments, the sections and apertures may have different cross sectional shapes that are complementary to the cross sectional shape of the accessories to be received therein. In alternative embodiments, the accessories can extend partially or completely through the supports.

As shown in FIGS. 1 and 6, the accessories 16 include an IV pole/handle device 182, an IV pole 184, an infusion pump 186 coupled to IV pole 184, an IV pole 188 (shown in phantom), an oxygen tank holder 190, and a handle 192. The IV pole/handle device 182 includes elongated inner and outer telescoping members 194, 196, a handle 198, and hooks 210. The outer member 196 of IV pole/handle device 182 is positioned in coupler 25 so that clamp 150 may compress outer member 196 to couple IV pole/handle device 182 to accessory supports 12, 14 as shown in FIGS. 1 and 3. The outer member 196 of IV pole/handle device 182 includes an aperture 197 in which inner member 194 of IV pole/handle device 182 is positioned as shown in FIG. 3.

The hooks 210 are configured to hold medical supplies and accessories such as IV solution containers. The hooks 210 are coupled to the upper end of inner member 194 so that the hooks 210 move with inner member 194 relative to outer member 196 between a lower position (shown in solid lines in FIG. 1) and an upper position (shown in phantom lines in FIG. 1).

The handle 198 includes a contoured grip portion 212 and a sleeve 214 that extends from grip portion 212 downwardly to accessory supports 12, 14. The grip portion 212 and sleeve 214 are positioned over outer member 196 of IV pole/handle device 182 as shown in FIGS. 1 and 3. The outer member 196 of IV pole/handle device 182 provides a structural member that permits a caregiver to grasp the grip portion 212 and push or maneuver bed 10. In preferred embodiments, the grip portion 212 and sleeve 214 are made of a resilient material such as rubber.

The oxygen tank holder 190 includes a coupler or rod 216 and a metal basket or oxygen tank support 218 as shown in FIG. 6. The metal basket 218 is configured to receive and support an oxygen tank 220 (in phantom). The rod 216 is coupled to an upper portion of the metal basket 218 and is configured to be positioned in one of the couplers 25, 26, 27 of accessory supports 12, 14.

The handle 192, shown in FIG. 6, includes a structural member 222, a grip portion 224, and a sleeve 226. The structural member 222 is configured to be positioned in couplers 25, 26, 27 so that handle 192 may be coupled to accessory supports 12, 14. The grip portion 224 and sleeve 226 are positioned around structural member 222. In preferred embodiments, the grip portion 224 and sleeve 226 are made from a resilient material, such as rubber, and the structural member 222 is made of a rigid metal material.

As shown in FIG. 1, bed 10 further includes end bumpers 228 and side bumpers 230 configured to minimize or prevent damage to walls, doors, and other objects when bed 10 is moved. Each of end bumpers 228 includes a roller 232 in a mounting bracket 234 that couples roller 232 to support coupling location 23 of frame 20. Each of the mounting brackets 234 include a pin or axle 236 about which rollers 232 are permitted to rotate. Side bumpers 230 each include rollers 242 coupled to pivot post 60 of accessory supports 12, 14 as shown, for example, in FIG. 3. The upper, lower, and side walls 72, 74, 76 of frame 20 define an opening 238 in which side bumper 230 is positioned as shown in FIG. 1. Each side bumper 230 includes an aperture 240 in which pivot post 60 and cylindrical sleeve 88 of bushing 87 are positioned. In preferred embodiments, the rollers 232, 242 are made of a rubber or plastics material.

Figure 7:
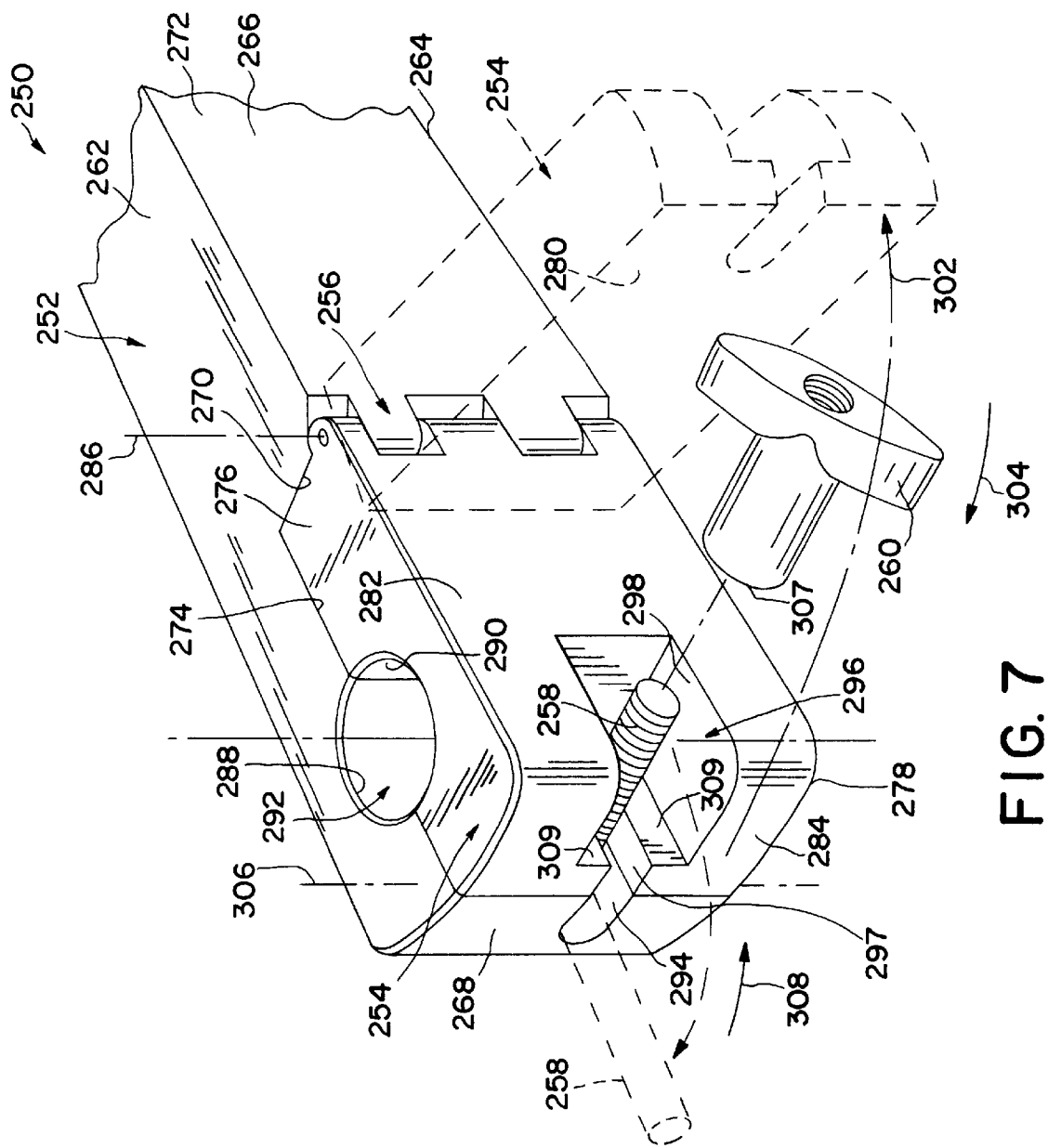
FIG. 7 is a perspective exploded view of an alternative embodiment accessory support.

Another embodiment of an accessory support 250 is shown in FIG. 7. Accessory support 250 includes a body 252, an arm 254, a hinge or coupler 256 that pivotably couples the arm 254 to body 252, a threaded stud 258 pivotably coupled to body 252, and a nut 260. The body 252 includes an upper surface 262, a lower surface 264, a side surface 266 extending between upper and lower surfaces 262, 264, and an end surface 268. The side surface 266 includes a step 270 separating the side surface 266 into first and second side surface portions 272, 274. The arm 254 is coupled to the body 252 at the intersection of the step 270 and first side surface portion 272. The arm 254 includes an upper surface 276, a lower surface 278, an inner side surface 280, an outer side surface 282, and an end surface 284.

The coupler 256 permits arm 254 to pivot about an axis 286 between a closed position (solid lines in FIG. 7) wherein arm 254 abuts body 252 and an open position (phantom lines in FIG. 7). In the closed position, the inner side surface 280 of arm 254 faces toward second side surface portion 274 of body 252. The body 252 and arm 254 each include semicircular-shaped recesses 288, 290, respectively, in the second side surface portion 274 of body 252 and inner side surface 280 of arm 254. In the closed position, the semicircular recesses 288, 290 of body 252 and arm 254, respectively, define a circular aperture 292 extending between upper and lower surfaces 262, 264 of body 252 and upper and lower surfaces 276, 278 of arm 254.

Body 252 further includes a stud-receiving aperture 294 in the end surface 268 of body 252. Arm 254 further includes an aperture 296 extending between inner and outer side surfaces 280, 282 of arm 254 and opening at end surface 284 of arm 254. The aperture 296 of arm 254 includes a first stud-receiving portion 297 and a second nut-receiving portion 298.

To couple an accessory 16 to accessory support 250, a caregiver moves arm 254 in direction 302 to its open position, places accessory 16 in semi-circular shaped recess 288 formed in body 252, moves arm 254 in direction 304 to its closed position to position accessory 16 in the aperture 292 defined by semicircular recesses 288, 290, moves threaded stud 258 about its pivot axis 306 in direction 308 through threaded stud-receiving aperture 294 formed in body 252 and threaded stud-receiving portion 297 of aperture 296 formed in arm 254, and threads nut 260 onto threaded stud 258 to fix the position of accessory 16 within accessory support 250. As the nut 260 is threaded onto stud 258, an end surface 307 of nut 260 abuts an inner surface 309 of arm 254. Once the nut 260 engages the surface 309 of arm 254, further rotation of the nut 260 to thread the nut 260 onto the stud compresses an accessory positioned between arm 254 and body 252. In FIG. 7, the arm 254 and body 252 are shown abutting each other when the arm is in its closed position. However, the accessory placed in aperture 292 may include a diameter larger than the diameter of aperture 292 of accessory support 250. When the arm 254 and body 252 cooperate to clamp such a larger diameter accessory, the arm 254 and body 252 clamp the accessory without abutting each other.

Accessory support 250 may include additional couplers such as couplers 25, 26, 27 of accessory supports 12, 14. In preferred embodiments, accessory support 250 includes a pivot post and latch or coupler similar to pivot post 60 and latch 62 of accessory support 12, 14 to couple accessory support 250 to frame 20.

Figure 8:
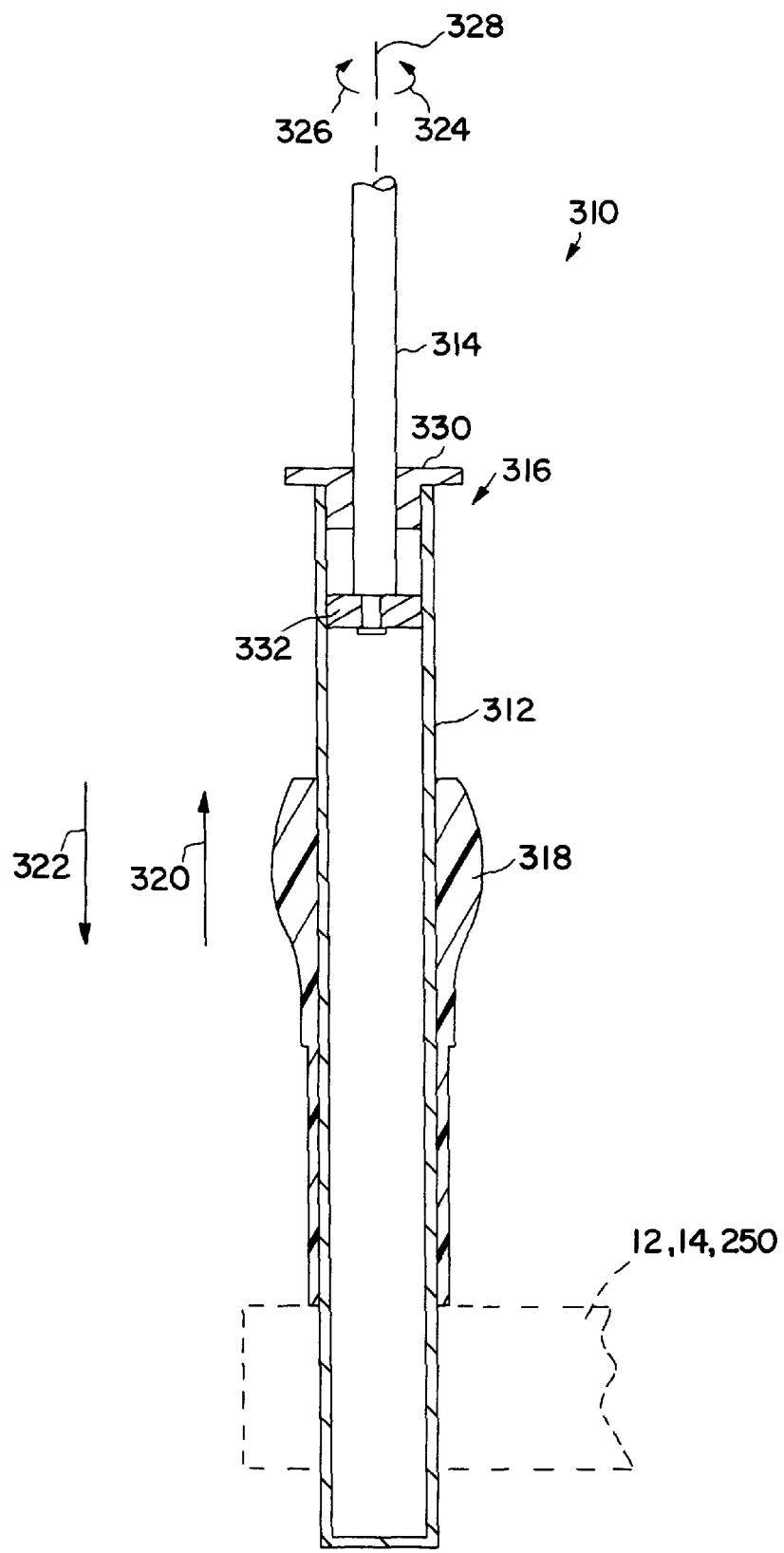
FIG. 8 is a sectional view of an alternative embodiment IV pole.

An alternative embodiment of an accessory 310 is shown in FIG. 8. Accessory 310 includes an outer telescoping member 312, an inner telescoping member 314, a coupler 316 configured to couple inner and outer telescoping members 312, 314, and a handle 318 positioned around outer telescoping member 312. Outer telescoping member 312 is configured to extend into and through an accessory support 12, 14, 250 as shown in FIG. 8.

The handle 318 slides freely on outer telescoping member 312 so that the handle 318 can be moved upwardly in direction 320, downwardly in direction 322, and rotated in directions 324, 326 about an axis 328. When a caregiver wants to move bed 10 using handle 318, the caregiver grasps handle 318, moves handle 318 to a desired location, and then applies force to handle 318 to move bed 10. The only limitations on the movement of handle 318 is the supports 12, 14, 250 which limit the amount of downward movement in direction 322 and a portion of coupler 316 positioned at the upper end of outer member 312 which limits the amount of upward movement in direction 320. Because handle 318 slides freely on outer member 312, when a caregiver is not using handle 318, the handle 318 moves downwardly in direction 322 under the force of gravity into contact with accessory support 12, 14, 250.

The coupler 316 permits inner telescoping member 314 to move axially in directions 320, 322 relative to outer telescoping member 312. In the illustrated embodiment, coupler 316 includes first and second portions 330, 332. First portion 330 is coupled to an upper end of outer telescoping member 312 and second portion 332 is coupled to a lower end of inner telescoping member 314. The coupler 316 selectively locks the position or movement of the inner and outer members 312, 314 by having the first portion 330 of coupler 316 movable between a first position clamping the inner member 314 and a second position unclamping the inner member 314. In alternative embodiments, the coupler includes structure at the lower end of the telescoping member which expands to abut the inner surface of the outer member to lock the position of the inner and outer members or contracts inwardly away from the outer member to permit relative movement of the inner and outer members.

Although the invention has been described in detail with reference to illustrated embodiments, variations and modifications exist within the scope and spirit of the invention as described and defined in the following claims.

What is claimed is:

1. An accessory support apparatus for use with a patient support, the accessory support apparatus comprising:
    a body, the body including a plurality of accessory couplers;
    a coupler configured to couple the body to the patient support for pivotable movement about an axis of rotation;
    a latch configured to lock the body selectively in one of a plurality of predetermined discretely spaced latch positions relative to the patient support; and
    wherein the plurality of predetermined discretely spaced latch position are arranged along a circular arc and the plurality of accessory couplers are configured to be indexed along the circular arc defined by the plurality of predetermined discretely spaced latch positions.

2. The apparatus of claim 1, wherein the plurality of accessory couplers includes a plurality of apertures formed in the body.

3. The apparatus of claim 1, wherein the plurality of accessory couplers includes a clamp.

4. An accessory support apparatus for use with a patient support, the accessory support apparatus comprising:
    a body, the body including a plurality of accessory couplers;
    a coupler configured to couple the body to the patient support for pivotable movement about an axis of rotation;
    a latch configured to lock the body selectively in one of a plurality of different positions relative to the patient support; and
    wherein the plurality of accessory couplers includes a pin.

5. The apparatus of claim 1, wherein the latch includes a spring-biased pin.

6. The apparatus of claim 1, further comprising a push handle coupled to one of the accessory couplers, push handle including a grip portion to permit a caregiver to move the patient support.

7. The apparatus of claim 6, further comprising an IV pole coupled to the push handle.

8. The apparatus of claim 7, wherein the push handle includes a first telescoping member and the IV pole includes a second telescoping member coupled to the first telescoping member to permit vertical adjustment of the IV pole relative to the push handle.

9. An accessory support apparatus for use with a patient support, the accessory support apparatus comprising:
    a body, the body including a plurality of accessory couplers;
    a coupler configured to couple the body to the patient support for pivotable movement about an axis of rotation;
    a latch configured to lock the body selectively in one of a plurality of predetermined discretely spaced positions relative to the patient support; and
    wherein the a coupler includes a pivot post coupled to the body and configured to extend through an aperture formed in the patient support.

10. The apparatus of claim 9, wherein the coupler further includes a clutch configured to couple the body to the patient support, clutch being configured to hold the body in a desired position with respect to the patient support and permit movement of the body relative to the patient support when a predetermined force is applied to the body.

11. The apparatus of claim 1, further comprising an accessory coupled to one of the plurality of accessory couplers, the accessory including at least one of an IV pole, an infusion pump, a tank holder, and a handle.

12. An accessory support apparatus for use with a patient support, the accessory support apparatus comprising:
    a body, the body including a plurality of accessory couplers;
    a coupler configured to couple the body to the patient support for pivotable movement about an axis of rotation;

a latch configured to lock the body selectively in one of a plurality of different positions relative to the patient support; and wherein the latch includes a locking pin configured to selectively engage one of a plurality of apertures formed in the patient support, and a spring configured to bias the locking pin to a locking position.

13. The apparatus of claim 12, further comprising a position pin coupled to the locking pin, the position pin being configured to hold the locking pin in an unlocked position when the position pin is in a first position relative to the body and to permit the locking pin to move to its locking position when the position pin is in a second position relative to the body.

14. The apparatus of claim 1, wherein the body includes an arm pivotably coupled to the body, the arm being movable relative to the body to provide a clamp mechanism.

15. The apparatus of claim 14, further comprising a fastener pivotably coupled to the body, the fastener being movable from a first position to permit the arm to move relative to the body to a second position to clamp the arm against the body.

16. The apparatus of claim 14, wherein the arm and the body cooperate to define an accessory receiving aperture therebetween.

17. The apparatus of claim 1, further comprising an accessory coupled to one of the plurality of accessory couplers, the accessory comprising a first member coupled to the body, a second member movably coupled to the first member, the second member including an item holder, and a handle coupled to the first member.

18. The apparatus of claim 17, wherein the first member is an outer telescoping member and the second member is an inner telescoping member which is movable relative to the outer telescoping member to adjust a position of the inner telescoping member.

19. The apparatus of claim 18, further comprising a coupler configured to lock a position of the inner telescoping member relative to the outer telescoping member.

20. The apparatus of claim 17, wherein the second member is an IV pole.

21. The apparatus of claim 17, wherein the handle is movable relative to the first member.

22. An apparatus for use with a patient support, the apparatus comprising:

an accessory support including a body, the body having an accessory coupler;

a coupler configured to couple the body to the patient support for pivotable movement about an axis of rotation;

a first member slidably received within the accessory coupler, the first member including a lower end and an upper end, the lower end being solely supported by the body of the accessory support for movement relative to the patient support;

a second member movably coupled to the first member, the second member including an item holder; and a handle coupled to the first member.

23. The apparatus of claim 22, wherein the first member is an outer telescoping member and the second member is an inner telescoping member which is movable relative to the outer telescoping member to adjust a position of the inner telescoping member.

24. The apparatus of claim 23, further comprising a coupler configured to lock a position of the inner telescoping member relative to the outer telescoping member.

25. The apparatus of claim 22, wherein the second member is an IV pole.

26. The apparatus of claim 22, wherein the handle is movable relative to the first member.

27. The apparatus of claim 26, further comprising a stop coupled to the first member, the handle being movable between the stop and the patient support.

28. The apparatus of claim 26, wherein the handle is configured to surround the first member, the handle being slidable over the first member to permit the caregiver to adjust a position of the handle to a desired position on the first member.

29. The apparatus of claim 22, wherein the handle is made from a resilient material.

30. The apparatus of claim 22, further comprising a body including a plurality of accessory couplers, and a coupler configured to couple the body to the patient support for pivotable movement about an axis of rotation, the first member being coupled to one of the plurality of accessory couplers of the body.

31. The apparatus of claim 30, further comprising a latch configured to lock the body selectively in one of a plurality of different positions relative to the patient support.

32. An apparatus for use with a patient support, the apparatus comprising:

a first member coupled to the patient support;

a second member movably coupled to the first member, the second member including an item holder;

a handle coupled to the first member;

a body including a plurality of accessory couplers;

a coupler configured to couple the body to the patient support for pivotable movement about an axis of rotation, the first member being coupled to one of the plurality of accessory couplers of the body;

a latch configured to lock the body selectively in one of a plurality of different positions relative to the patient support; and wherein the latch includes a locking pin configured to selectively engage one of a plurality of apertures formed in the patient support, and a spring configured to bias the locking pin to a locking position.

33. The apparatus of claim 32, further comprising a position pin coupled to the locking pin, the position pin being configured to hold the locking pin in an unlocked position when the position pin is in a first position relative to the body and to permit the locking pin to move to its locking position when the position pin is in a second position relative to the body.

34. An apparatus for use with a patient support, the apparatus comprising:

a first member coupled to the patient support;

a second member movably coupled to the first member, the second member including an item holder;

a handle coupled to the first member;

a body including a plurality of accessory couplers;

a coupler configured to couple the body to the patient support for pivotable movement about an axis of rotation, the first member being coupled to one of the plurality of accessory couplers of the body; and wherein the coupler further includes a clutch configured to couple the body to the patient support, the clutch being configured to hold the body in a desired position with respect to the patient support and permit movement of the body relative to the patient support when a predetermined force is applied to the body.

35. The apparatus of claim 30, wherein the body includes an arm pivotably coupled to the body, the arm being movable relative to the body to provide a clamp mechanism to secure the first member to the body.

36. An apparatus for use with a patient support, the apparatus comprising:

a push handle including a grip portion;

a coupler configured to movably couple the push handle to the patient support, such that the grip portion is positionable to permit a caregiver to move the patient support;

an IV pole coupled to the push handle; and a latch configured to lock the push handle selectively in one of a plurality of predetermined discretely spaced latch positions relative to the patient support.

37. The apparatus of claim 36, wherein the push handle includes an outer telescoping member and the IV pole is an inner telescoping member which is movable relative to the outer telescoping member to adjust a position of the inner telescoping member relative to the push handle.

38. The apparatus of claim 37, wherein the push handle includes a grip portion which is movable relative to the outer telescoping member.

39. The apparatus of claim 38, further comprising a stop coupled to the outer telescoping member, the grip portion being movable between the stop and the patient support.

40. The apparatus of claim 36, further comprising a body coupled to the push handle, the coupler being configured to couple the body to the patient support for pivotable movement about an axis of rotation, and further comprising a latch configured to lock the body selectively in one of a plurality of different positions relative to the patient support.

* * * * *